United States Patent
Hallinan et al.

(10) Patent No.: US 9,790,159 B2
(45) Date of Patent: *Oct. 17, 2017

(54) CATALYST STABILITY AND CORROSION PREVENTION IN ACETIC ACID PRODUCTION PROCESS

(71) Applicant: LyondellBasell Acetyls, LLC, Houston, TX (US)

(72) Inventors: Noel C. Hallinan, Loveland, OH (US); Brian A. Salisbury, Houston, TX (US); Daniel F. White, Houston, TX (US); David L. Ramage, Houston, TX (US); Jared T. Fern, Houston, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,683

(22) Filed: Sep. 22, 2016

(65) Prior Publication Data

US 2017/0008827 A1  Jan. 12, 2017

Related U.S. Application Data

(63) Continuation of application No. 14/492,529, filed on Sep. 22, 2014, now Pat. No. 9,475,746.

(51) Int. Cl.
*C07C 51/12* (2006.01)
*B01J 27/20* (2006.01)

(52) U.S. Cl.
CPC .............. *C07C 51/12* (2013.01); *B01J 27/20* (2013.01)

(58) Field of Classification Search
CPC ................................ C07C 51/12; B01J 27/20
See application file for complete search history.

(56) References Cited

U.S. PATENT DOCUMENTS

| 5,817,869 | A | 10/1998 | Hinnenkamp et al. |
| 7,083,831 | B1 | 8/2006 | Koch et al. |
| 9,475,746 | B2 * | 10/2016 | Hallinan ................ B01J 27/20 |
| 2012/0095259 | A1 | 4/2012 | Salisbury et al. |
| 2013/0102809 | A1 | 4/2013 | Le Berre et al. |
| 2013/0102810 | A1 | 4/2013 | Le Berre et al. |
| 2013/0165688 | A1 | 6/2013 | Le Berre et al. |

OTHER PUBLICATIONS

International Search Report and Written Opinion for PCT/US2015/051211 dated Nov. 26, 2015.

* cited by examiner

*Primary Examiner* — Clinton Brooks
*Assistant Examiner* — Ana Z Muresan

(57) ABSTRACT

Processes for producing acetic acid herein generally include contacting methanol and carbon monoxide in the presence of a reaction medium under carbonylation conditions sufficient to form acetic acid, the reaction medium including a carbonylation catalyst selected from rhodium catalysts, iridium catalysts and palladium catalysts; from 1 wt. % to 14 wt. % water; and a plurality of additives, in-situ generated derivatives of the plurality of additives or combinations thereof; the plurality of additives including a first additive including one or more phosphine oxides and a second additive selected from heteropolyacids, metal salts and combinations thereof, the heteropolyacids represented by the formula $H_nM_{12}XO_{40}$, wherein H is hydrogen, M is selected from tungsten and molybdenum, X is selected from phosphorous and silicon and O is oxygen and n is 3 or 4, the metal salts are selected from transition metal salts, lanthanide metal salts and combinations thereof; and recovering acetic acid from the process.

1 Claim, 3 Drawing Sheets

CATALYST STABILITY AND CORROSION PREVENTION IN ACETIC ACID PRODUCTION PROCESS

CROSS-REFERENCE TO RELATED APPLICATIONS

This application is a continuation application of U.S. patent application Ser. No. 14/492,529, filed Sep. 22, 2014, the disclosure of which is incorporated herein by reference in its entirety.

STATEMENT REGARDING FEDERALLY SPONSORED RESEARCH OR DEVELOPMENT

Not applicable.

BACKGROUND

Field

The present disclosure generally relates to acetic acid production processes. In particular, embodiments contained herein relate to additives for acetic acid production processes.

Related Art

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Acetic acid may be commercially produced by methanol carbonylation. Methanol carbonylation processes often utilize a promoter, such as methyl iodide, in addition to carbonylation catalyst. A consequence of iodide promoted reactions is that, in addition to the added alkyl iodide, variable concentrations of in-situ generated hydrogen iodide may be present. Unfortunately, hydrogen iodide is highly corrosive. Continuous efforts have been directed towards reducing corrosion in acetic acid production processes.

Contained herein are embodiments directed to resolving, or at least reducing, one or all of the problems mentioned above.

SUMMARY

Embodiments disclosed herein include processes for producing acetic acid. In one or more embodiments, the processes generally include contacting methanol and carbon monoxide in the presence of a reaction medium under carbonylation conditions sufficient to form acetic acid, wherein the reaction medium includes a carbonylation catalyst selected from rhodium catalysts, iridium catalysts and palladium catalysts; from 1 wt. % to 14 wt. % water; and a plurality of additives, in-situ generated derivatives of the plurality of additives or combinations thereof; wherein the plurality of additives include a first additive and a second additive; wherein the first additive includes one or more phosphine oxides; and the second additive is selected from heteropolyacids, metal salts and combinations thereof, wherein the heteropolyacids are represented by the formula $H_nM_{12}XO_{40}$, wherein H is hydrogen, M is selected from tungsten and molybdenum, X is selected from phosphorous and silicon and O is oxygen and n is 3 or 4, the metal salts are selected from transition metal salts, lanthanide metal salts and combinations thereof; and recovering acetic acid from the process.

One or more embodiments include the process of the preceding paragraph, wherein the one or more phosphine oxides are independently selected from non-benzoyl containing pentavalent phosphine oxides, compound mixtures of at least four phosphine oxides and pentavalent aryl or alkaryl phosphine oxides including one or more benzoyl groups; wherein the non-benzoyl containing pentavalent phosphine oxides have the formula $R_3P=O$, wherein each R is independently selected from substituted or unsubstituted alkyls, aryls, aralkyls and combinations thereof; and wherein each phosphine oxide of the compound mixtures has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof and wherein each phosphine oxide has at least 15 carbon atoms.

One or more embodiments include the process of any preceding paragraph, wherein the one or more heteropolyacids are selected from 12-tungstophosphoric acid, 12-tungstosilicic acid, 12-molybdophosphoric acid, 12-molybdosilicic acid and combinations thereof.

One or more embodiments include the process of any preceding paragraph, wherein the second additive includes the heteropolyacid and the reaction medium includes a second additive concentration of from 0.005 mol/L to 0.05 mol/L.

One or more embodiments include the process of any preceding paragraph, wherein the second additive includes the metal salt and the reaction medium includes a second additive concentration of from 0.005 mol/L to 0.25 mol/L.

One or more embodiments include the process of any preceding paragraph, wherein the metal salt is selected from zinc acetate (ZnOAc), chromium (III) tri chloride ($CrCl_3$), chromium (III) acetate hydroxide (CrOAcOH), lanthanide acetate (LaOAc), zirconium hydroxide (ZrOH), yttrium acetate (YOAc) and combinations thereof.

One or more embodiments include the process of any preceding paragraph, wherein the plurality of additives include greater than 50 mol. % first additive.

One or more embodiments include the process of any preceding paragraph, wherein the plurality of additives include from 10 mol. % to less than 50 mol. % second additive.

One or more embodiments include the process of any preceding paragraph, wherein the plurality of additives include greater than 50 mol. % second additive.

One or more embodiments include the process of any preceding paragraph, wherein the first additive and the second additive are introduced into the reaction medium nearly simultaneously.

One or more embodiments include the process of any preceding paragraph, wherein the acetic acid is glacial acetic acid.

One or more embodiments include the process of any preceding paragraph, wherein the reaction medium includes from 1 wt. % to 10 wt. % water.

One or more embodiments include the process of any preceding paragraph, wherein the reaction medium includes from 1 wt. % to 6 wt. % water.

One or more embodiments include the process of any preceding paragraph, wherein the reaction medium includes a first additive concentration of from 0.005 mol/L to 2.0 mol/L.

One or more embodiments include the process of any preceding paragraph, wherein the carbonylation conditions include a temperature of from 150° C. to 250° C. and a pressure of from 200 psig to 2000 psig.

One or more embodiments include the process of any preceding paragraph exhibiting a corrosion rate that is from 5% to 100% less than that of an identical process absent the second additive.

One or more embodiments include the process of any preceding paragraph exhibiting a corrosion rate that is at least 75% less than that of an identical process absent the second additive.

One or more embodiments include the process of any preceding paragraph further exhibiting a catalyst stability that is equal to or greater than that of an identical process absent the plurality of additives.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWING

The claimed subject matter may be understood by reference to the following description taken in conjunction with the accompanying drawings, in which like reference numerals identify like elements, and in which:

Figure 1:
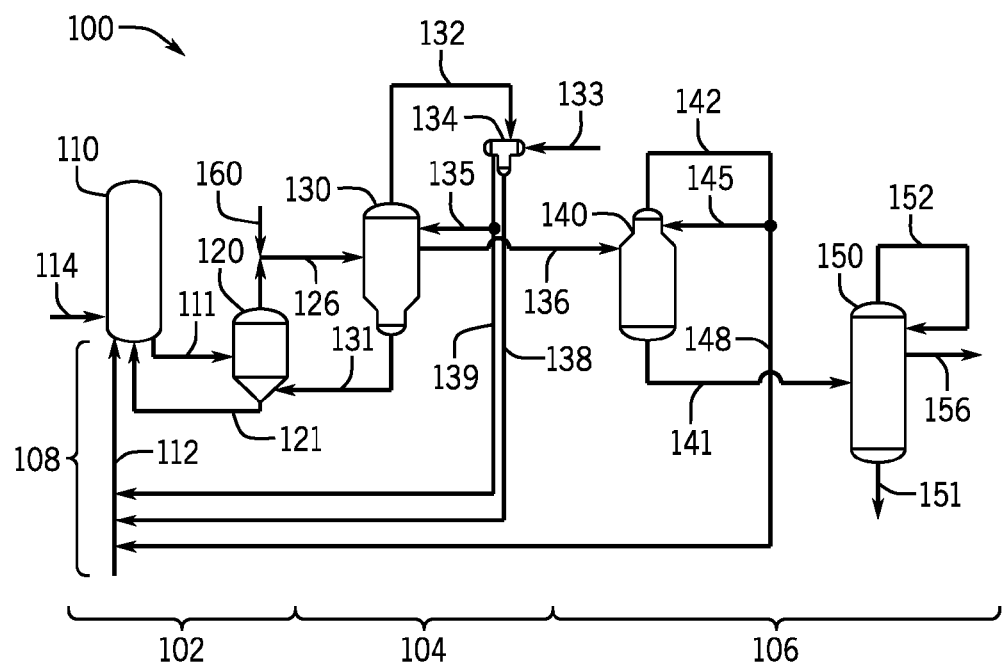
FIG. 1 illustrates a schematic of one or more embodiments of the disclosed process.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

In the description below, unless otherwise specified, all compounds described herein may be substituted or unsubstituted and the listing of compounds includes derivatives thereof. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments described herein generally include processes for producing carboxylic acids. It will be realized that while specific embodiments herein may refer to acetic acid (often referred to as HOAc) production processes, it is to be understood by one skilled in the art that such embodiments may be utilized in other carboxylic acid production processes. Furthermore, one or more specific embodiments include production of glacial acetic acid (which is encompassed by the term "acetic acid" as referenced herein). Glacial acetic acid refers to acetic acid that is generally undiluted (includes a water concentration at most in the parts per million range).

The acetic acid production processes generally include carbonylation processes. For example (and for purposes of discussion herein), the acetic acid production processes may include the carbonylation of methanol or its derivatives to produce acetic acid. As referenced previously herein, the embodiments described herein are also applicable to the carbonylation of higher homologues of methanol, such as ethanol, butanol and pentanol, for example, to produce acids which are higher homologues of acetic acid. The adaptation of the embodiments to such systems will be readily apparent to the artisan given the following discussion.

Carbonylation processes generally include reacting an alcohol, such as methanol, with carbon monoxide in a liquid reaction medium under carbonylation conditions sufficient to form acetic acid and recovering the formed acetic acid from the process.

The reaction medium generally includes a carbonylation catalyst. Suitable carbonylation catalysts include those known in the art, such as rhodium catalysts, iridium catalysts and palladium catalysts. Suitable rhodium catalysts include rhodium metal and rhodium compounds selected from rhodium salts, rhodium oxides, rhodium acetates, organo-rhodium compounds, coordination compounds of rhodium and mixtures thereof, for example. (See, U.S. Pat. No. 5,817,869, which is incorporated in its entirety herein.) Suitable iridium catalysts include iridium metal and iridium compounds selected from acetates, oxalates, acetoacetates and mixtures thereof, for example. (See, U.S. Pat. No. 5,932,764, which is incorporated in its entirety herein.)

The concentration of carbonylation catalyst utilized in the reaction medium may be from 1 mmol to 100 mmol, or from 2 mmol to 5 mmol, or at least 7.5 mmol, or from 2 mmol to 75 mmol, or from 5 mmol to 50 mmol, or from 7.5 mmol to 25 mmol of catalyst per liter of reaction medium, for example.

In one or more embodiments, the carbonylation catalyst is utilized with a co-catalyst. The co-catalyst may include those known in the art. For example, the co-catalyst may be selected from metal and metal compounds selected from osmium, rhenium, ruthenium, cadmium, mercury, zinc, gallium, indium, tungsten and mixtures thereof.

In one or more embodiments, the reaction medium includes from 2 wt. % to 14 wt. %, or 10 wt. % or less, or 8 wt. % or less, or 6 wt. % or less, or from 1 wt. % to 5 wt. %, or from 4 wt. % to 8 wt. % water based on the total weight of the reaction medium, for example. However, utilization of iodide promoter within the reaction medium can result in in-situ generation of hydrogen iodide. Unfortunately, hydrogen iodide can be corrosive and therefore may be undesirable in the carbonylation process.

The reaction medium may further include a variety of additives or other components (i.e., components other than the alcohol, carbon monoxide and carbonylation catalyst). The introduction of such additives to the reaction medium can be via any method known in the art. For example, each of the additives may be, either independently or as a mixture, introduced directly to the reaction medium. Alternatively, one or more of the additives may be generated in-situ, for example.

In the embodiments described herein, the additives include a plurality of additives. The plurality of additives includes a first additive(s) and a second additive(s). The first additive generally includes one or more phosphine oxides, while the second additive is generally selected from heteropolyacids, metal salts and combinations thereof.

The one or more phosphine oxides, in one or more embodiments, are represented by the formula $R_3PO$, where R is alkyl or aryl, O is oxygen, P is phosphorous. In one or more embodiments, the one or more phosphine oxides include a compound mixture of at least four phosphine oxides, where each phosphine oxide has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof. Each phosphine oxide has at least 15, or at least 18 total carbon atoms.

Examples of suitable phosphine oxides for use in the compound mixture include, but are not limited to, tri-n-hexylphosphine oxide (THPO), tri-n-octylphosphine oxide (TOPO), tris(2,4,4-trimethylpentyl)-phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo[3.3.1]nonane-9-oxide, dihexylmonooctylphosphine oxide, dioctylmonohexylphosphine oxide, dihexylmonodecylphosphine oxide, didecylmonohexylphosphine oxide, dioctylmonodecylphosphine oxide, didecylmonooctylphosphine oxide, and dihexylmonobutylphosphine oxide and the like.

The compound mixture includes from 1 wt. % to 60 wt. %, or from 35 wt. % to 50 wt. % of each phosphine oxide based on the total weight of compound mixture. In one or more specific, non-limiting embodiments, the compound mixture includes TOPO, THPO, dihexylmonooctylphosphine oxide and dioctylmonohexylphosphine oxide. For example, the compound mixture may include from 40 wt. % to 44 wt. % dioctylmonohexylphosphine oxide, from 28 wt. % to 32 wt. % dihexylmonooctylphosphine oxide, from 8 wt. % to 16 wt. % THPO and from 12 wt. % to 16 wt. % TOPO, for example.

In one or more embodiments, the compound mixture exhibits a melting point of less than 20° C., or less than 10° C., or less than 0° C., for example.

In one or more specific embodiments, the compound mixture is Cyanex 923, commercially available from Cytec Corporation.

Each individual component of the compound mixture is solid while the mixture is liquid at room temperature. As used herein, "room temperature" means that a temperature difference of a few degrees does not matter to the phenomenon under investigation, such as a preparation method. In some environments, room temperature may include a temperature of from about 20° C. to about 28° C. (68° F. to 82° F.), while in other environments, room temperature may include a temperature of from about 50° F. to about 90° F., for example. However, room temperature measurements generally do not include close monitoring of the temperature of the process and therefore such a recitation does not intend to bind the embodiments described herein to any predetermined temperature range.

Mixtures and methods of forming such compound mixtures are described in U.S. Pat. No. 4,909,939, which is incorporated in its entirety herein.

In one or more embodiments, the one or more phosphine oxides include a pentavalent aryl or alkaryl phosphine oxide containing one or more benzoyl groups (i.e., benzoyl containing phosphine oxide). These benzoyl groups may be substituted or unsubstituted, for example. In one or more embodiments, the benzoyl containing phosphine oxide may be selected from bis(2,4,6-trimethylbenzoyl) phenyl phosphine oxide (BAPO), (2,4,6-trimethylbenzoyl) diphenyl phosphine oxide (TMDPO) or combinations thereof, for example. While the one or more additives are introduced to the reaction medium, it should be noted that the additives may react with components within the reaction medium and the additives, the in-situ generated components or combinations thereof may function as a corrosion inhibitor. Accordingly, the reaction medium may include the components introduced thereto (e.g., the benzoyl group containing phosphine oxide), any in-situ generated related components due to reaction, such as hydrolysis, and combinations thereof.

In one or more embodiments described herein, the one or more phosphine oxides include a pentavalent phosphine oxide (for ease of reference herein and to distinguish from prior referenced benzoyl containing pentavalent phosphine oxides, these compounds will be referred to herein as non-benzoyl group containing pentavalent phosphine oxides). The non-benzoyl containing pentavalent phosphine oxides generally have the formula $R_3P=O$, wherein each R is independently selected from substituted or unsubstituted alkyls, aryls, aralkyls and combinations thereof. For example, each R may be independently selected from methyl, ethyl, propyl, isopropyl, butyl, isobutyl, t-butyl, amyl, pentyl, hexyl, octyl, phenyl, naphthyl and combinations thereof, for example. When substituted, each substituent on each R group may be independently selected from those defined herein above for R, as well as halogens, hydroxyl groups, nitrogen groups, amino groups and combinations thereof, for example. Specific, non-limiting embodiments include triethyl phosphine oxide, tributyl phosphine oxide, tripentyl phosphine oxide, diphenylmethyl phosphine oxide, triphenyl phosphine oxide and combinations thereof for example. In one or more specific embodiments, the non-benzoyl containing pentavalent phosphine oxides include a phenyl group directly bonded to the phosphorous atom. In one or more specific embodiments, the non-benzoyl containing pentavalent phosphine oxides are selected from tri-butyl phosphine oxide (TBPO), tri-phenyl phosphine oxide (TPPO) and combinations thereof.

As discussed previously herein, the plurality of additives further includes a second additive selected from heteropolyacids, metal salts and combinations thereof. Heteropolyacids (HPA's) are generally a class of complex proton acids formed of a metal, oxygen, an element generally from the p-block of the periodic table and acidic hydrogen atoms. The hetero atom in the heteropoly acid may be selected from copper, beryllium, zinc, nickel, phosphorus, silicon, boron, aluminum, germanium, gallium, iron, cerium, cobalt, arsenic, antimony, bismuth, chromium, tin, titanium, zirconium, vanadium, sulfur, tellurium, manganese, platinum, thorium, hafnium, iodine and combinations thereof, for example. The polyatom may be selected from molybdenum, tungsten, vanadium, chromium, niobium, tantalum and combinations thereof, for example. The heteropolyacids may include, but are not limited to, phosphomolybdic acid ($H_3[PO_4(MO_2O_6)_6]xH_2O$) also known as PMA, tungstosilicic acid ($H_4SiW_{12}O_{40}H_2O$) also known as TSA, tungstophosphoric acid ($H_3[P(W_3O_{10})_4]xH_2O$) also known as PTA, molybdosilicic acid ($H_4SiMo_{12}O_{40}xH_2O$), molybdophosphoric acid ($H_3PMo_{12}O_{40}xH_2O$), molybdotungstophosphoric acid ($H_3[PMo_nW_{12-n}O_{40}]xH_2O$), molybdotungstosilicic acid ($H_4[SiMo_nW_{12-n}O_{40}]xH_2O$), vanadotungstophosphoric acid ($H_{3+n}[PV_nW_{12-n}O_{40}]$), vanadotungstosilicic acid ($H_{4+n}[SiV_nW_{12-n}O_{40}]xH_2O$), vanadomolybdosilicic acid ($H_{4+n}[SiV_nMO_{12-n}O_{40}]xH_2O$), vanadomolybdophosphoric acid ($H_{3+n}[PV_nMo_{12-n}O_{40}]xH_2O$, wherein n is an integer of 1 to 11 and x is an integer of 1 or more), tungstoboric acid ($H_5BW_{12}O_{40}$), molybdoboric acid ($H_5BMo_{12}O_{40}$) and molybdotungstoboric acid ($BH_5Mo_6O_{40}W_6$).

In one or more specific embodiments, the heteropolycyclic acid includes a phosphorus or silicon hetero atom and at least one polyatom selected from tungsten, molybdenum, chromium, vanadium, tantalum and combinations thereof. For example, the heteropolyacids may generally represented by the formula $H_nM_{12}XO_{40}$, wherein H is hydrogen, M is selected from tungsten and molybdenum, X is selected from phosphorous and silicon and O is oxygen and n is 3 or 4.

In one or more specific embodiments, the heteropolyacids may be selected from 12-tungstophosphoric acid, 12-tungstosilicic acid, 12-molybdophosphoric acid, 12-molybdosilicic acid and combinations thereof.

The metal salts are generally selected from transition metal salts, lanthanide metal salts and combinations thereof. The transition metal salts generally include a transition metal, such as a Group IIIB to Group IIB metals. For example, the transition metal may be selected from titanium, vanadium, chromium, manganese, iron, cobalt, nickel, copper, yttrium, zirconium, molybdenum, ruthenium, lanthanum, hafnium, tungsten, platinum, zinc, beryllium, aluminum, strontium, indium, tin, barium, and bismuth. In one or more embodiments, the metal salt is selected from zinc acetate (ZnOAc), chromium (III) tri chloride ($CrCl_3$), chromium (III) acetate hydroxide (CrOAcOH), lanthanide acetate (LaOAc), zirconium hydroxide (ZrOH) and yttrium acetate (YOAc), for example.

The plurality of additives may be introduced into the reaction medium in the form of a mixture (with or without additional additives therein) or they may be introduced to the reaction medium separately. However, it is contemplated within the embodiments described herein that at least a portion of the first additive and at least a portion of the second additive contact the reaction medium nearly simultaneously. Those skilled in the art of acetic acid processing via methanol carbonylation will appreciate that corrosion is a relatively slow process and that the order of addition of first and second additive is not of great importance so long as there is not a long period between the separate additions. For optimal corrosion inhibition, the additives should be added nearly simultaneously, where this term refers to up to about 2 weeks between the separate additions.

It should be understood that the effect of additives may range from those that allow substantially improved catalyst stabilization and substantially improved corrosion inhibition, to those that principally allow substantially improved catalyst stabilization and to those that principally allow improved corrosion inhibition, for example. Such improvements (decreased corrosion &/or improved catalyst stability) are possible while achieving acceptable, if not exceptional, rates of reaction.

While the plurality of additives are introduced to the reaction medium, it should be noted that the additives may react with components within the reaction medium and the additives, the in-situ generated components or combinations thereof may function as a corrosion inhibitor. Accordingly, the reaction medium may include the components introduced thereto (e.g., the plurality of additives), any in-situ generated related components due to reaction, such as hydrolysis, and combinations thereof.

The concentration of the plurality of additives introduced into the reaction medium, as well as the individual components thereof, should be sufficient to provide an improvement in corrosion inhibition, catalyst stabilization or a combination thereof. The exact concentration of the total plurality of additives, as well as the concentration of the first additive and the second additive will depend on the specific process conditions, including the particular additives utilized. However, in one or more embodiments, the concentration of the one or more phosphine oxides introduced into the reaction medium may vary from 0.005M to 2.0M, or from 0.02M to 1.0M, or from 0.3M to 0.5M, for example. In such embodiments, the heteropolyacid concentration introduced into the reaction medium may vary from 0.005M to 0.05M, or from 0.0025M to 0.04M, or from 0.003M to 0.04M, for example. Further, in such embodiments, the metal salt concentration introduced into the reaction medium may vary from 0.005M to 0.25M, or from 0.05M to 0.20M, or from 0.1M to 0.18M, for example.

In one or more embodiments, the plurality of additives includes greater than 50 mol. %, or at least 60 mol. %, or at least 70 mol. %, or at least 80 mol. %, or at least 90 mol. %, or at least 95 mol. %, or at least 97 mol. %, or at least 98 mol. %, or at least 99 mol. % first additive, for example. In one or more embodiments, the plurality of additives includes greater than 50 mol. %, or at least 60 mol. %, or at least 70 mol. %, or at least 80 mol. %, or at least 90 mol. %, or at least 95 mol. %, or at least 97 mol. %, or at least 98 mol. %, or at least 99 mol. % second additive, for example. In one or more embodiments, the plurality of additive include at least 10 mol. %, or at least 20 mol. % or from 10 mol. % to 50 mol. % second additive, for example. In alternative embodiments, the at least two additives are utilized in essentially equal amounts.

It has been observed that the use of the plurality of additives described herein inhibits corrosion at an unexpected rate. For example, the process may exhibit corrosion at a rate (measured as described in the examples that follow herein) that is at least 50%, or at least 60%, or at least 70%, or at least 75%, or at least 80%, or at least 85%, or at least 90%, or at least 95% less than that of an identical process absent the plurality of additives as disclosed herein. It has further been observed that the process may exhibit corrosion of 15% or less, or 10% or less, or 5% or less, or 2% or less. In fact, corrosion rates of 0% may be possible with the embodiments described herein.

It has further been observed that utilizing the plurality of additives described herein provides an order of magnitude further decrease in corrosion rate than utilizing either of the additives alone. For example, utilizing the second additive alone provides little to no benefit in corrosion resistance (and may even increase corrosion) while utilizing the first and second additives in combination provide for a 5% to 100%, or at least 75%, or at least 80% increase in corrosion resistance to utilizing the first additive (the one or more phosphine oxides) alone. Furthermore, it has been observed that such corrosion rate can occur at a secondary additive concentration as low as 0.01M, for example.

It has further been observed that such decreased corrosion can be obtained without decreased catalyst stability. Measurement of catalyst stability is measured as described in the Examples below. In fact, it has been observed that an improvement in catalyst stability may be possible when utilizing the plurality of additives rather than utilizing either the first or second additive alone. For example, utilizing the second additive alone provides little to no benefit in catalyst stability (and may even decrease catalyst stability) while utilizing the first and second additives in combination provide for a 5% to 100%, or at least 75%, or at least 80% increase in corrosion resistance to utilizing the first additive (the one or more phosphine oxides) alone.

The reaction medium may further include an alkyl iodide, such as methyl iodide, for example. The concentration of alkyl iodide in the reaction medium may be from 0.6 wt. % to 36 wt. %, or from 4 wt. % to 24 wt. %, or from 6 wt. % to 20 wt. % based on total weight of reaction medium, for example. Furthermore, the reaction medium may include an alkyl acetate, such as methyl acetate, for example. The concentration of alkyl acetate in the reaction medium may be from 0.6-36, or 2 wt. % to 20 wt. %, or from 2 wt. % to 16 wt. %, or from 3 wt. % to 10 wt. %, or from 2 wt. % to 8 wt. % based on the total weight of the reaction medium, for example. As described previously herein, the introduction of such components to the reaction medium can be via any method known in the art including introduction to the reaction medium or in-situ generation, for example.

It is contemplated that supplemental hydrogen may be supplied to the reaction medium. Supplemental hydrogen may be supplied to the reaction medium to provide a total hydrogen concentration in the reaction medium of from 0.1 mol. % to 5 mol. %, or from 0.3 mol. % to 3 mol. %, for example.

In practice, carbonylation reaction conditions vary depending upon reaction parameters, reactor size and charge and the individual components employed. However, in one or more embodiments, the carbonylation process may be a batch or continuous processes and the carbonylation conditions may include a pressure of from 200 psig to 2000 psig, or from 200 psig to 1000 psig, or from 300 psig to 500 psig, for example and a temperature of from 150° C. to 250° C., or from 170° C. to 220° C. or from 150° C. to 200° C., for example.

Carbonylation processes further include recovering the formed acetic acid from the process. Such recovery can be accomplished by methods known in the art and may include, without limitation, separation and/or purification processes (including but not limited to flashing and distillation). Such processes are known to one skilled in the art and therefore are not described in detail herein.

FIG. 1 illustrates a schematic of an embodiment of an acetic acid production process 100. The process 100 is generally described in terms of functional areas, i.e., a reaction area 102, a light-ends area 104, a purification area 106 and a recycle area 108, rather than specific process equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and flash vessel 120. For example, the reaction area 102 may include reactor 110, flash vessel 120, and streams (or portions of streams) 111, 112, 114, 121, 126, 131, 160, 138, 139, 148. The reactor 110 is a reactor or vessel in which methanol is carbonylated in the presence of a catalyst to form acetic acid at elevated pressure and temperature. The flash vessel 120 is a tank or vessel in which a reaction mixture obtained in the reactor, for example the reactor 110, is at least partially depressurized and/or cooled to form a vapor stream and a liquid stream.

The light-ends area 104 may include a separations column, for example, a light-ends column 130, equipment associated with light-ends column 130, and streams associated with the light-ends column 130. For example, the light-ends area 104 may include light-ends column 130, decanter 134, and streams 126, 131, 132, 133, 135, 136, 138, 139, 160. The light-ends column 130 is a fractioning or distillation column and includes any equipment associated with the column, including but not limited to heat exchangers, decanters, pumps, compressors, valves, and the like.

The purification area 106 may include a drying column 140, optionally, a heavy-ends column 150, equipment associated with drying column 140 and heavy-ends column 150, and streams associated with the drying column 140 and heavy-ends column 150. For example, the purification area 106 may include drying column 140, heavy-ends column 150, and streams 136, 141, 142, 145, 148, 151, 152, 156. The heavy-ends column 150 is a fractioning or distillation column and includes any equipment associated with the column, including but not limited to heat exchangers, decanters, pumps, compressors, valves, and the like.

The recycle area 108 may include process streams recycled to the reaction area 102 and/or light-ends area 104. For example, in FIG. 1, the recycle area 108 may include streams 121, 138, 139, 148.

In an embodiment, the reactor 110 may be configured to receive a carbon monoxide feed stream 114 and a methanol or methanol/methyl acetate feed stream 112. A reaction mixture may be withdrawn from the reactor in stream 111. Other streams may be included as known in the art, for example, a stream that may recycle a bottoms mixture of the reactor 110 back into the reactor 110, or a stream may be included to release a gas from the reactor 110. Stream 111 may include at least a part of the reaction mixture.

In an embodiment, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110 (stream 121 may thus be considered in the recycle area 108 and in the reactor area 102). In an embodiment, stream 126 may comprise acetic acid, water, methyl iodide, methyl acetate, HI, and mixtures thereof.

In an embodiment, the light-ends column 130 may include a distillation column and equipment associated with the distillation column including but not limited to a heat exchanger 137, a decanter 134, pumps, compressors, valves, and other related equipment. The light-ends column 130 may be configured to receive stream 126 from the flash vessel 120. Stream 132 includes overhead product from the light-ends column 130, and stream 131 includes bottoms product from the light-ends column 130. Light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor (stream 138 may thus be considered in the recycle area 108, in the light-ends area 104, and in the reactor area 102). Stream 139 may recycle a portion of the light phase of decanter 134 back to the reactor 110 via, for example, stream 112 (stream 139 may thus be considered in the recycle area 108, in the light-ends area 104, and in the reactor area 102). Stream 136 may emit from the light-ends column 130. Other streams may be included as known in the art, for example, a stream that may recycle a bottoms mixture of the light-ends column 130 back into the light-ends column 130. Any stream received by or emitted from the light-ends column 130 may pass through a pump, compressor, heat exchanger, and the like as is common in the art.

In an embodiment, the drying column 140 may comprise a vessel and equipment associated with the vessel including but not limited to heat exchangers, decanters, pumps, compressors, valves, and the like. The drying column 140 may be configured to receive stream 136 from the light-ends column 130. The drying column 140 may separate components of stream 136 into streams 142 and 141.

Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment known in the art, for example, a heat exchanger or separation vessel before streams 145 or 148 recycle components of stream 142. Other streams may be included as known in the art, for example, a stream may recycle a bottoms mixture of the drying column 140 back into the drying column 140. Any stream received by or emitted from the drying column 140 may pass through a pump, compressor, heat exchanger, separation vessel, and the like as is common in the art.

The heavy-ends column 150 may include a distillation column and equipment associated with the distillation column including but not limited to heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 140. Stream 156 may include acetic acid product.

Suitable alternative embodiments for the acetic acid production system 100 may be found in U.S. Pat. No. 6,552,221, which is herein incorporated by reference.

EXAMPLES

To facilitate a better understanding of the disclosure, the following examples of embodiments are given. In no way should the following examples be read to limit, or to define, the scope of the appended claims.

CORROSION STUDY TEST PROCEDURE: Prepared samples were added to 5 mL heavy walled borosilicate Wheaton vials such that the vials contained a total liquid volume of 4 mL. A glass bead blasted 316L stainless steel coupon of dimensions 0.062"×0.30"×0.50" and of approximately 1 gram in weight was added to each vial. Prior to addition to the vial, the coupons were cleaned by immersion in acetone for 5 minutes, followed by drying and weighing on a 4-figure analytical balance. These vials, charged with liquid and coupon, were then septum sealed and purged with one atmosphere of CO or $N_2$ for 2 minutes followed by placement in a water bath maintained at the specified temperature. After 44-48 hours of heating, the vials were removed from the water bath and allowed to cool. The coupons were removed, soaked in acetone for 5 minutes, dried and re-weighed.

Figure 2:
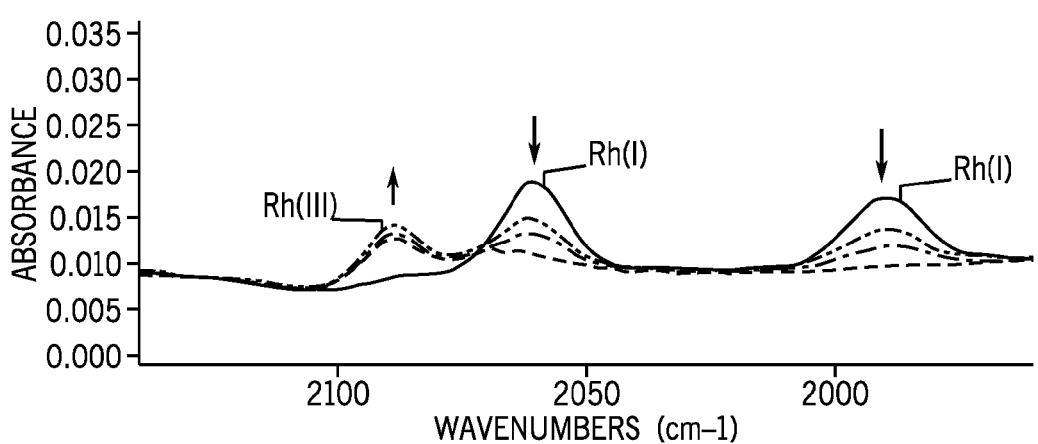
FIG. 2 illustrate Rh(I) and Rh(III) spectra.

CATALYST STABILITY TEST PROCEDURE: Studies were undertaken to analyze catalyst stability in terms of extent of decay of soluble Rh(I) to Rh(III). The rate and extent of Rh(I) decay in catalyst solutions maintained under flash tank conditions can be monitored by periodic sampling and FTIR analysis. In such a procedure, a stock solution of the active rhodium catalyst was prepared by adding 0.20 g of rhodium (I) dicarbonyl chloride dimer, to 20 mLs of acetic acid and saturating the solution with CO by bubbling one atmosphere of CO through the solution at room temperature for 5 minutes. 0.40 g of lithium iodide was then added and after 10 minutes of stirring, the active Rh catalyst, $[Rh(CO)_2I_2]^-$ formed in quantitative yield. In the present examples, a solution of about 5,000 PPM resulted. For catalyst stability studies, aliquots of this solution were then added to solutions contained in septum sealed vials of the type described in Corrosion Study Test Procedure. Overlaid spectra in FIG. 2 show this behavior for the case of no promoter being present where over the course of a one hour monitoring period, Rh(I) decays completely to Rh(III).

A number of experiments were undertaken to determine the effectiveness of a variety of additives on corrosivity and catalyst stability. Unless specified otherwise, all corrosion studies were performed under the following conditions: 1 atm CO, 44 hours, 70° C., 0.5 M HI, 3.2M $H_2O$, HOAc. Unless specified otherwise, all catalyst stability studies were performed under the following conditions: 1 atm $N_2$, 70° C., 0.1M HI, 2.0M $H_2O$, HOAc, 2500 ppm Rh.

Numerous samples were prepared and studied for corrosion. Results of testing on a variety of HPA's as well as a control sample, are shown in Table 1 below.

TABLE 1

| Additive | Conc (M) | Corrosion (% loss) |
|---|---|---|
| None | N/A | 0.414 |
| TSA | 0.017 | 0.505 |
| TSA | 0.034 | 0.548 |
| PTA | 0.004 | 0.493 |
| PTA | 0.017 | 0.564 |
| PTA | 0.047 | 0.694 |

The data show that the sampled heteropolycyclic acids (HPA) showed no ability to decrease corrosion rate relative to the condition where no additive was present. In fact, the reverse was true and corrosion rate increased with increasing HPA concentration.

In contrast, Table 2 illustrates corrosion rates that, in most cases, are dramatically decreased for combinations of HPA's with phosphine oxides. Further, corrosion rates, in most cases, are significantly lower than for phosphine oxides as a single additive, indicating that a synergistic effect may be operation.

TABLE 2

| First Additive | Conc (M) | Second Additive | Conc (M) | Corrosion (% loss) |
|---|---|---|---|---|
| TPPO | 1.00 | none | N/A | 0.070 |
| TPPO | 0.97 | TSA | 0.004 | 0.018 |
| TPPO | 0.98 | TSA | 0.009 | 0.027 |
| TPPO | 0.98 | TSA | 0.023 | 0.000 |
| TPPO | 1.00 | TSA | 0.046 | 0.009 |

TABLE 2-continued

| First Additive | Conc (M) | Second Additive | Conc (M) | Corrosion (% loss) |
|---|---|---|---|---|
| Cyanex ®923 | 1.00 | none | N/A | 0.232 |
| Cyanex ®923 | 1.00 | TSA | 0.018 | 0.189 |
| BAPO | 0.010 | TSA | 0.018 | 0.018 |
| BAPO | 0.010 | none | N/A | 0.412 |
| TBPO | 1.00 | TSA | 0.017 | 0.264 |
| TBPO | 0.98 | none | N/A | 0.281 |
| TBPO | 0.99 | TSA | 0.005 | 0.225 |
| TBPO | 1.10 | TSA | 0.008 | 0.153 |
| TBPO | 0.99 | TSA | 0.020 | 0.181 |
| TPPO | 1.00 | PTA | 0.040 | 0.099 |
| Cyanex ®923 | 0.98 | PTA | 0.0177 | 0.253 |
| TBPO | 1.00 | PTA | 0.0186 | 0.216 |

Figure 3:
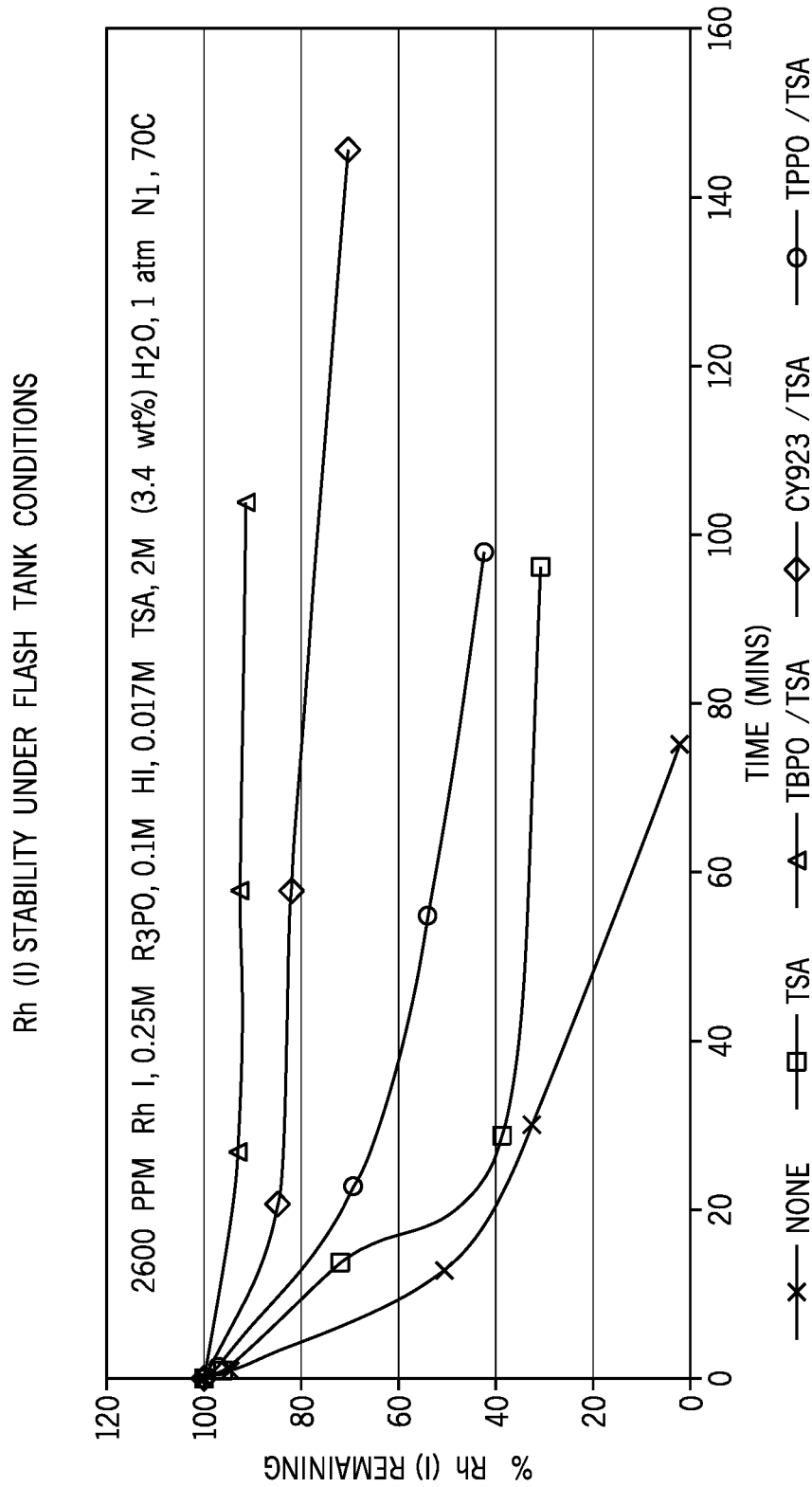
FIGS. 3-4 illustrates time profiles for Rh(I) decay for various additive samples.
Figure 4:
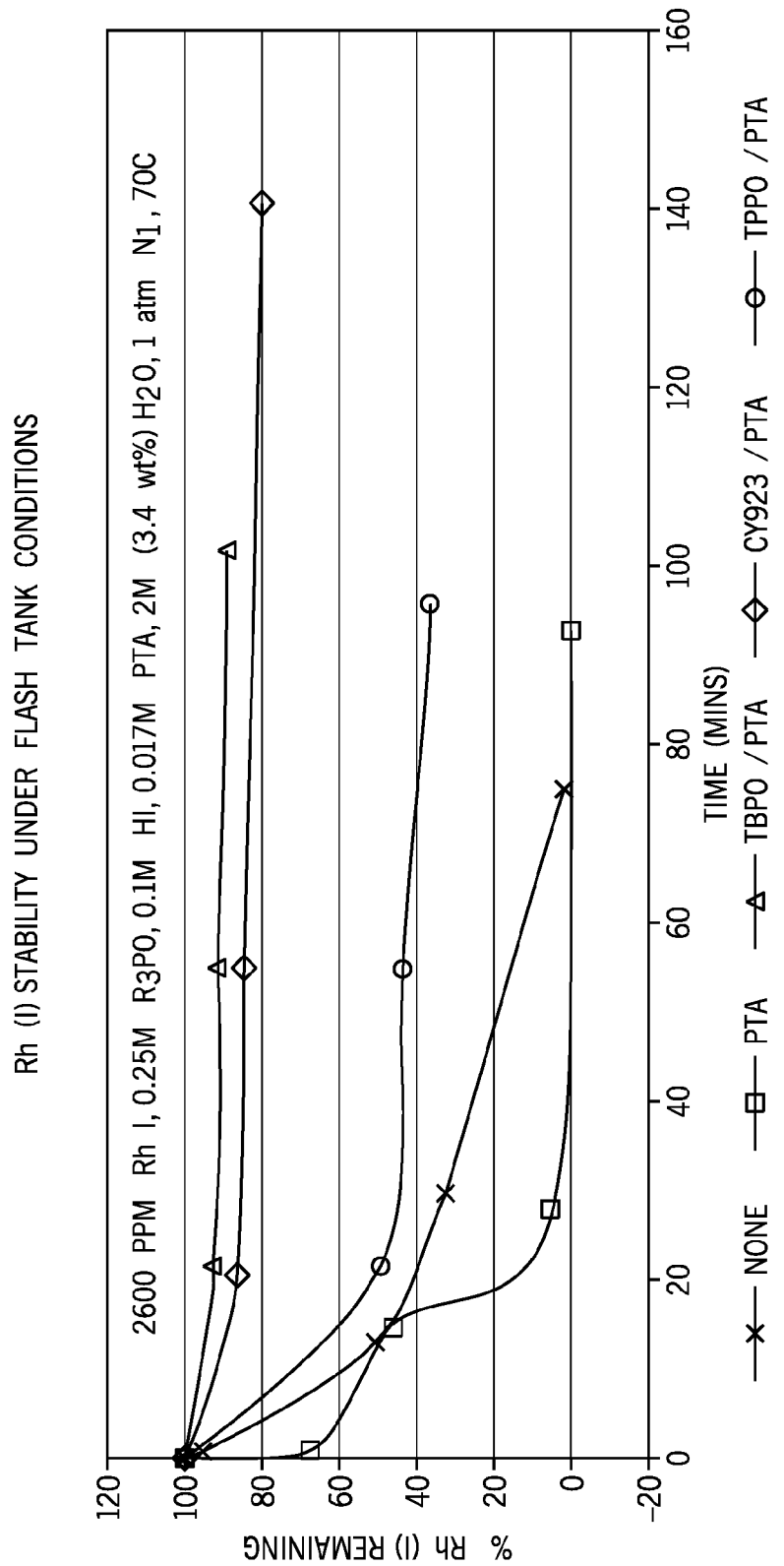

Time profiles for Rh(I) decay for various TSA/R$_3$PO and PTA/R$_3$PO mixtures are shown in FIGS. 3 and 4. Consistent with the dramatically improved corrosion rates observed above for HPA/R$_3$PO mixtures relative to one HPA, catalyst stability also shows a similar directional improvement for most samples with the extent of stabilization being a function of R$_3$PO basicity.

In order to put these and other data on a quantitative footing, % Rh(I) remaining at the one hour mark was chosen and an infrared spectrum of each experiment obtained at this time point. Catalyst stability data from these experiments are shown in Table 3.

TABLE 3

| First Additive | Conc (M) | Second Additive | Conc (M) | % Rh(I) @ 1 hr |
|---|---|---|---|---|
| None | N/A | none | N/A | 9 |
| None | N/A | TSA | 0.017 | 35 |
| None | N/A | PTA | 0.017 | 0 |
| TPPO | 0.250 | none | N/A | 64 |
| TPPO | 0.250 | TSA | 0.017 | 53 |
| TPPO | 0.250 | PTA | 0.017 | 43 |
| Cyanex ®923 | 0.250 | none | N/A | 80 |
| Cyanex ®923 | 0.250 | TSA | 0.017 | 82 |
| Cyanex ®923 | 0.250 | PTA | 0.017 | 87 |
| TBPO | 0.250 | none | N/A | 95 |
| TBPO | 0.250 | TSA | 0.017 | 92 |
| TBPO | 0.250 | PTA | 0.017 | 95 |

Similar studies were carried out as described above for HPA's for metal salts, as described herein and below. For the sake of simplicity, salts such as Cr(III) acetate are written as CrOAc. The corrosion data in Table 4 below indicate little evidence for any corrosion suppression in the presence of these metal salts. In fact, in most cases, there is an increase in extent of corrosion.

TABLE 4

| Additive | Conc (M) | Corrosion (% loss) |
|---|---|---|
| None | N/A | 0.414 |
| ZnOAc | 0.1 | 0.619 |
| ZnOAc | 0.2 | 0.252 |
| CrCl$_3$ | 0.1 | 0.578 |
| CrCl$_3$ | 0.2 | 0.629 |
| CrOAcOH | 0.1 | 0.650 |
| CrOAcOH | 0.2 | 0.361 |
| LaOAc | 0.1 | 0.523 |
| LaOAc | 0.2 | 0.375 |
| ZrOH | 0.1 | 0.492 |
| ZrOH | 0.2 | 0.547 |
| YOAc | 0.1 | 0.528 |
| YOAc | 0.2 | 0.412 |

Table 5 indicates that when BAPO is added to the metal salts, in most cases, an order of magnitude less of BAPO in terms of concentration, leads to an order of magnitude decrease in corrosion rate. Note that Amberlyst™ 15 is an ion exchange resin commercially available from Rohm and Haas, Co.

TABLE 5

| First Additive | Conc (M) | Second Additive | Conc (M) | Corrosion (% loss) |
|---|---|---|---|---|
| None | N/A | None | N/A | 0.101 |
| BAPO | 0.01 | None | N/A | 0.018 |
| BAPO | 0.01 | ZnOAc | 0.1 | 0.009 |
| BAPO | 0.01 | CrCl$_3$ | 0.1 | 0.072 |
| BAPO | 0.01 | LaOAc | 0.1 | 0.027 |
| BAPO | 0.01 | YOAc | 0.1 | 0.054 |
| BAPO | 0.01 | Amberlyst ™ 15 | 0.1 | 3.334 |

Data from these experiments, which were widely spaced in time, show an unambiguous and consistent trend in which extent of corrosion is always greatest when no additive is present. For comparative purposes and to ensure maximum accuracy, a control vial containing no additive was generally included in every run. Therefore, data sometimes includes slightly differing values for the control experiment.

Related catalyst stability studies with some of these metal salts showed that, for the most part, they provide good catalyst stabilization under flash tank conditions. This catalyst stabilization is not compromised by the addition of BAPO and in fact, a slight improvement in catalyst stability is observed in metal salt/BAPO mixtures, as shown in Table 6.

TABLE 6

| First Additive | Conc (M) | Second Additive | Conc (M) | % Rh(I) @ 1 hr |
|---|---|---|---|---|
| None | N/A | None | N/A | 9 |
| BAPO | 0.01 | None | N/A | 22 |
| BAPO | 0.01 | ZnOAc | 0.25 | 88 |
| BAPO | 0.01 | YOAc | 0.25 | 95 |
| BAPO | 0.01 | LaOAc | 0.25 | 94 |
| None | N/A | ZnOAc | 0.25 | 79 |
| None | N/A | YOAc | 0.25 | 84 |
| None | N/A | LaOAc | 0.25 | 89 |

Therefore, the embodiments as disclosed herein are well adapted to attain the ends and advantages mentioned as well as those that are inherent therein. The particular embodiments disclosed above are illustrative only, as such they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the appended claims. Accordingly, the protection sought herein is as set forth in the claims below.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

What is claimed is:

1. A process for producing acetic acid comprising:
   a) contacting methanol and carbon monoxide in the presence of a reaction medium under carbonylation conditions sufficient to form acetic acid, wherein the reaction medium comprises:
      i) a rhodium (I) catalyst;
      ii) 1-14 wt. % water; and
      iii) a first additive comprising the general formula $R_3P=O$, where R is an aryl or an alkyl group, a second additive selected from the group consisting of 12-tungstophosphoric acid, 12-tungstosilicic acid, 12-molybdophosphoric acid, 12-molybdosilicic acid and combinations thereof;
   b) recovering acetic acid,
   wherein the process exhibits a corrosion rate that is at least 75% less than that of an identical process absent the second additive.

* * * * *

UNITED STATES PATENT AND TRADEMARK OFFICE
CERTIFICATE OF CORRECTION

PATENT NO. : 9,790,159 B2  
APPLICATION NO. : 15/272683  
DATED : October 17, 2017  
INVENTOR(S) : Noel C. Hallinan et al.

It is certified that error appears in the above-identified patent and that said Letters Patent is hereby corrected as shown below:

In the Specification

| | | |
|---|---|---|
| Column 6 | Line 47 | After "thereof", insert --,-- |
| Column 7 | Line 10 | Delete "($H_{3+n}[PV_nW_{12-n}O_{40}]$)," and insert --($H_{3+n}[PV_nW_{12-n}O_{40}]$),-- |
| Column 7 | Line 11 | Delete "($H_{4+n}[SiV_nMO_{12-n}O_{40}]xH_2O$)," and insert --($H_{4+n}[SiV_nMo_{12-n}O_{40}]xH_2O$),-- |
| Column 11 | Line 44 | Delete "140." and insert --130.-- |

In the Claims

| | | |
|---|---|---|
| Column 15 | Line 22 | In Claim 1, after "thereof;", insert --and-- |

Signed and Sealed this  
Fourteenth Day of April, 2020

Andrei Iancu  
*Director of the United States Patent and Trademark Office*